(12) United States Patent
Lang et al.

(10) Patent No.: US 7,597,893 B2
(45) Date of Patent: Oct. 6, 2009

(54) **HUMAN MONOCLONAL ANTIBODY SPECIFIC LIPOPOLYSACCHARIDES (LPS) OF SEROTYPE IATS 06 OF *PSEUDOMONAS AERUGINOSA***

(75) Inventors: Alois B. Lang, Helmberg (CH); Michael P. Horn, Thun (CH); Martin A. Imboden, Münsingen (CH)

(73) Assignee: Kenta Biotech AG (CH)

( * ) Notice: Subject to any disclaimer, the term of this patent is extended or adjusted under 35 U.S.C. 154(b) by 342 days.

(21) Appl. No.: 11/271,008

(22) Filed: Nov. 10, 2005

(65) Prior Publication Data

US 2006/0093610 A1    May 4, 2006

Related U.S. Application Data

(63) Continuation of application No. PCT/EP2004/004485, filed on Apr. 28, 2004.

(51) Int. Cl.
*A61K 39/40* (2006.01)
*A61K 39/395* (2006.01)
*A61K 39/00* (2006.01)

(52) U.S. Cl. ............. 424/150.1; 424/130.1; 424/133.1; 424/137.1; 424/141.1; 424/142.1; 424/164.1; 424/170.1; 424/178.1; 530/809

(58) Field of Classification Search ............. 424/130.1, 424/133.1, 137.1, 141.1, 142.1, 150.1, 164.1, 424/170.1, 178.1; 530/809
See application file for complete search history.

(56) References Cited

U.S. PATENT DOCUMENTS 4,834,975 A    5/1989    Siadak et al.

FOREIGN PATENT DOCUMENTS

| EP | 0 441 395 | 8/1991 |
|---|---|---|
| WO | 02/20619 | 3/2002 |

OTHER PUBLICATIONS

Cryz, S.J. et al., "Safety and Immunogenicity of a *Pseudomonas aeruginosa* O-Polysaccharide Toxin A Conjugate Vaccine in Humans," *Journal of Clinical Investigation*, vol. 80(1), pp. 51-56, 1987.

Hemachandra, S. et al., "Human Monoclonal Antibodies Against *Pseudomonas aeruginosa* Lipopolysaccharide Derived from Transgenic Mice Containing Megabase Human Immunoglobulin Loci are Opsonic and Protective Against Fatal *Pseudomonas sepsis*," *Infection and Immunity*, vol. 69(4), pp. 2223-2229, 2001.

Persic et al., "An Integrated Vector System for the Eukaryotic Expression of Antibodies or Their Fragments After Selection from Phage Display Libraries," *Gene*, vol. 187(1), pp. 9-18, 1997.

*Primary Examiner*—Rodney P. Swartz
(74) *Attorney, Agent, or Firm*—Drinker Biddle & Reath LLP

(57) ABSTRACT

The present application relates to a human monoclonal antibody specific for the serotype IATS 06 of *P. aeruginosa*, a hybridoma producing it, nucleic acids encoding it, and host cells transfected therewith. Further, the present invention relates to methods for producing said monoclonal antibody. In addition, the present invention relates to pharmaceutical compositions comprising at least one antibody or at least one nucleic acid encoding said antibody.

21 Claims, 5 Drawing Sheets

Fig 1.

```
5' CAG GCG CAG CTG GTG CAG TCT GGG GCT GAA GTG AAG AAG CCT GGG GCC TCA GTG    54
   Gln Ala Gln Leu Val Gln Ser Gly Ala Glu Val Lys Lys Pro Gly Ala Ser Val    18

CDR1
   AAG GTC TCC TGT AAG GCT TCT GGA TAC ACC TTC ATC GGC TAT TGG ATG CAC TGG   108
   Lys Val Ser Cys Lys Ala Ser Gly Tyr Thr Phe Ile Gly Tyr Trp Met His Trp    36

GTG CGA CAG GCC CCT GGA CAA GGG CCT GAG TGG ATG GGA CGG ATC AAC CCT AAC   162
   Val Arg Gln Ala Pro Gly Gln Gly Pro Glu Trp Met Gly Arg Ile Asn Pro Asn    54

CDR2
   AGT GGT GGC ACA AAG TAT GTA CAG AAG TTT CAG GGC AGG GTC ACC GTG ACC AGG   216
   Ser Gly Gly Thr Lys Tyr Val Gln Lys Phe Gln Gly Arg Val Thr Val Thr Arg    72

GAC ACG TCC ATC AGC ACA GCC TAC ATG GAG CTG AAC TGG CTG ACA TCT GAC GAC   270
   Asp Thr Ser Ile Ser Thr Ala Tyr Met Glu Leu Asn Trp Leu Thr Ser Asp Asp    90

CDR3
   ACG GCC GTC TAT TAC TGT GCG AGA GCA AGG CCT GGT TGT GGT GGT GAT TGC TAT   324
   Thr Ala Val Tyr Tyr Cys Ala Arg Ala Arg Pro Gly Cys Gly Gly Asp Cys Tyr   108

GAG GTC TTA GAT TAC TGG GGC CAG GGA ACC CTG GTC ACC GTC TCC TCA 3'        369
   Glu Val Leu Asp Tyr Trp Gly Gln Gly Thr Leu Val Thr Val Ser Ser           123
```

Fig 2.

```
5' GAC ATC CAG ATG ACC CAG TCT CCT TCC ACC CTG TCT GCA TCT GTA GGA GAC AGA    54
   Asp Ile Gln Met Thr Gln Ser Pro Ser Thr Leu Ser Ala Ser Val Gly Asp Arg    18

CDR1
   GTC ACC ATC ACT TGC CGG GCC AGT CAG AGT ATT AGT AGC TGG TTG GCC TGG TAT   108
   Val Thr Ile Thr Cys Arg Ala Ser Gln Ser Ile Ser Ser Trp Leu Ala Trp Tyr    36

CDR2
   CAG CAG AAA CCA GGG AAA GCC CCT AAG CTC TTG ATC TAT AAG GCA TCT AGT TTA   162
   Gln Gln Lys Pro Gly Lys Ala Pro Lys Leu Leu Ile Tyr Lys Ala Ser Ser Leu    54

GAA AGT GGG GTC CCA TCA AGG TTC AGC GGC AGT GGA TCT GGG ACA GAA TTC ACT   216
   Glu Ser Gly Val Pro Ser Arg Phe Ser Gly Ser Gly Ser Gly Thr Glu Phe Thr    72

CTC ACC ATT AGC AGC CTG CAG CCT GAT GAT TTT GCA ACT TAT TAC TGC CAA CAG   270
   Leu Thr Ile Ser Ser Leu Gln Pro Asp Asp Phe Ala Thr Tyr Tyr Cys Gln Gln    90

CDR3
   TAT AAA AGT TAT CCC GTG TTT GGC CAA GGG ACC AAG GTG GAA ATC AAA GGA 3'   321
   Tyr Lys Ser Tyr Pro Val Phe Gly Gln Gly Thr Lys Val Glu Ile Lys Gly       107
```

Fig 3
a.
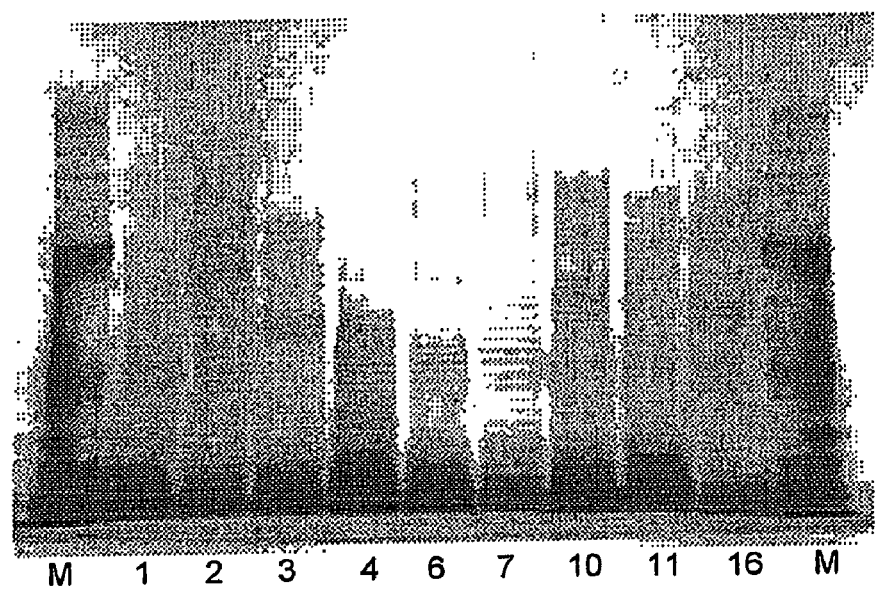
b.
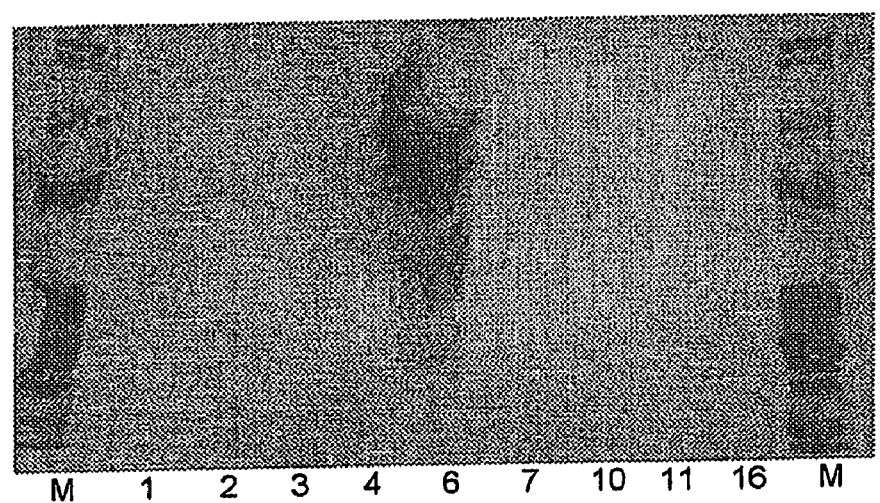

HUMAN MONOCLONAL ANTIBODY SPECIFIC LIPOPOLYSACCHARIDES (LPS) OF SEROTYPE IATS 06 OF *PSEUDOMONAS AERUGINOSA*

The present application is a continuation of International Patent Application No. PCT/EP2004/004485, filed Apr. 28, 2004, which claims priority to European Patent Application No. 03 010 836.9, filed on May 14, 2003, all of which are hereby incorporated by reference in their entirety herein.

The present invention relates to a human monoclonal antibody specific for the serotype IATS O6 of *P. aeruginosa*, a hybridoma producing it, nucleic acids encoding it, and host cells transfected therewith. Further, the present invention relates to methods for producing said monoclonal antibody. In addition, the present invention relates to pharmaceutical compositions comprising at least one antibody or at least one nucleic acid encoding said antibody.

Infectious diseases emerged drastically during the last decades. Infectious diseases, including respiratory infections, are one of the world's leading causes of illness. In 1998, infectious diseases claimed 16 million lives and ranked as the world's second leading cause of death. One of the biggest problems are hospital-acquired or nosocomial infections. Such infections have increased from 7.2/1000 patient days in 1975 to 9.8/1000 patient days in 1995, an increase of 36%. Together with methicillin-resistant *S. aureus* (MRSA) and vancomycin-resistant enterococci (VRE), *P. aeruginosa* is responsible for up to 34% of all nosocomial infections. Main victims of *P. aeruginosa* infections are cystic fibrosis patients, burn victims, intubated patients, patients in intensive care units, cancer and AIDS patients, as well as immunosuppressed patients having undergone organ transplantation.

For the prevention of chronic *P. aeruginosa* infections in cystic fibrosis patients, an octavalent conjugate-vaccine consisting of the 8 most relevant LPS serotypes of *P. aeruginosa* coupled to detoxified Toxin A of *P. aeruginosa* has been established for active immunization. Long-term studies with this vaccine have shown that the ratio of chronically infected patients dropped from about 72% to 32% at the age of 18 years. However, active vaccination is only possible in immunocompetent patients, as well as in predictable situations. Thus, most of the *P. aeruginosa* victims cannot be immunized actively with the octavalent vaccine. Due to this and due to the fact that most *P. aeruginosa* strains are multi-drug resistant, there is a need for an alternative therapeutic tool to treat *P. aeruginosa-infected* patients. One attempt is to create human monoclonal antibodies on the basis of hybridoma technology or using the phage display repertoire cloning.

Both methods and the antibodies created thereby show serious drawbacks. The hybridoma technology is based on the eliciting of murine B cells of desired specificity by immunization with an antigen of choice and immortalization by fusion with a myeloma partner, which is the classical "Kohler and Milstein" approach. Thereafter, the genetic information of an antibody-producing clone can be recloned and humanized, either by CDR-grafting or phage display technology.

It is known that murine monoclonal antibodies directed to bacterial LPS recognize other epitopes than human antibodies. Therefore, generation of monoclonal antibodies in mice followed by humanization would not necessarily result in the isolation of antibodies with specificity of interest for the use in humans. There have been different attempts in generating human monoclonal antibodies to LPS moieties of *P. aeruginosa*. However, many of them lack effector functions and thus were not protective.

Accordingly, one technical problem underlying the present invention is to provide a human monoclonal antibody specific to LPS of a particular serotype of *P. aeruginosa* wherein the antibody exhibits high protective capacity, in particular in vivo.

The technical problem is solved by the human monoclonal antibodies as defined in the following.

According to the present invention, a human monoclonal antibody specific for LPS of the *P. aeruginosa* serotype IATS O6 is provided wherein the variable region of the light chain of the antibody comprises at least one of SEQ ID NO:1 in the CDR1 region, SEQ ID NO:2 in the CDR2 region and SEQ ID NO:3 in the CDR3 region, and wherein the variable region of the heavy chain of the antibody comprises at least one of SEQ ID NO:4 in the CDR1 region, SEQ ID NO:5 in the CDR2 region and SEQ ID NO:6 in the CDR3 region; or a fragment or derivative thereof capable of binding to said LPS.

The present invention further provides a hybridoma capable of producing the monoclonal antibody and nucleic acids encoding the light and heavy chain of the antibody, respectively. Further, the present invention provides vectors and host cells, comprising the nucleic acid. In addition, methods for producing the monoclonal antibodies are provided. In addition, pharmaceutical compositions comprising at least one antibody and/or at least one nucleic acid and second medical uses thereof are provided.

Surprisingly, it has been found that the human monoclonal antibodies according to the invention exhibit high protective capacity. In particular, the human monoclonal antibody proved to be opsonophagocytic in vitro. Even more important, the monoclonal antibodies according the present invention exhibit in vivo protective capacity as determined by the protection of sepsis in the murine burn wound model as shown in the examples.

According to the present invention the antibody is specific for the LPS of *P. aeruginosa* serotype IATS O6 and exhibits a value of opsonophagocytosis as determined by using fluorescence-conjugate bacteria of less than 0.01 pg/ml. No prior art antibody has been reported exhibiting an opsonophagocytic activity.

Contrary to prior art antibodies, the monoclonal antibody according to the present invention recognizes clinical isolates with high specificity. 38 of 38 samples of patients infected with *P. aeruginosa* of the IATS O6 serotype were identified using this antibody. Without being bound by theory, it is assumed that the monoclonal antibody is capable of recognizing each of the subtypes of IATS O 6 known in the prior art. This property renders the antibody particularly useful for diagnosis and therapy. Thus, the antibody according to the present invention exhibits an insurmountable reliability.

The term "human monoclonal antibody" as used herein encompasses any partially or fully human monoclonal antibody independent of the source from which the monoclonal antibody is obtained. The production of the human monoclonal antibody by a hybridoma is preferred. The monoclonal antibody may also be obtained by genetic engineering and in particular CDR grafting of the CDR segments as defined in the claims onto available monoclonal antibodies by replacing the CDR regions of the background antibody with the specific CDR segments as defined in the claims.

The term "CDR region" means the complementarity determining region of an antibody, i.e. the region determining the specificity of an antibody for a particular antigen. Three CDR regions (CDR1 to CDR3) are responsible for antigen binding on the heavy chain.

The positions of the CDR regions within the heavy chain are as follows:

CDR1 region amino acids 31 to 35 within the $V_H$ exon
CDR2 region amino acids 50 to 65 within the $V_H$ exon
CDR3 region amino acids 95 and following amino acids within the $V_H$ exon The positions of the CDR regions are independent from the class of antibody, i.e. IgM, IgA of IgG.

The positions of the CDR regions of the kappa light chain are as follows:
CDR1 region amino acids 24 to 34 within the $V_\kappa$ exon
CDR2 region amino acids 50 to 56 within the $V_\kappa$ exon
CDR3 region amino acids 89 and following amino acids within the $V_\kappa$ exon The positions of the CDR region within the lambda type light chain are as follows:
CDR1 region amino acids 23 to 36 within the $V_\lambda$ exon
CDR2 region amino acids 49 to 60 within the $V_\lambda$ exon
CDR3 region amino acids 88 and following amino acids within the $V_\lambda$ exon Amino acid alignments of the $V_H$, $V_\kappa$ and $V\lambda$ exon can be obtained from V base index. (found at Universal Resource Locator (URL): vbase.mrc-cpe.cam.ac.uk/).

The term "serotype" means any known serotype of P. aeruginosa. A concordance table of the different nomenclatures presently used for different P. aeruginosa serotypes is shown in table 1 in the specification.

The term "fragment" means any fragment of the antibody capable of binding to the LPS serotype. The fragment has a length of at least 10, preferably 20, more preferably 50 amino acids. It is preferred that the fragment comprises the binding region of the antibody. It is preferred that the fragment is a Fab or F(ab')$_2$ fragment or a mixture thereof.

The term "derivative" encompasses any muteins of the human monoclonal antibody differing by the addition, deletion, and/or substitution of at least one amino acid. Preferably, the derivative is a mutein of the human monoclonal antibody wherein the mutein carries at least one conservative substitution in any of the CDR's in the heavy chain and/or light chain as indicated in the claims. More preferably, the mutein has not more than 5, particularly preferred not more than 2 conservative substitutions. The capacity of the fragment or derivative of the antibody to bind to the particular LPS serotype is determined by direct ELISA as described in the material and methods section: the particular LPS is immobilized on the solid phase of ELISA plates. Antibody fragments or derivative of the antibodies are incubated with the immobilized LPS, and bound antibodies or derivatives thereof are visualized by a suitable enzyme-conjugated secondary antibody.

In accordance with the present invention, the term "conservative substitution" means a replacement of one amino acid belonging to a particular physico-chemical group with an amino acid belonging to the same physico-chemical group. The physico-chemical groups are defined as follows:

The group of non-polar amino acids comprises: glycine, alanine, valine, leucine, isoleucine, methionine, proline, phenylalanine, and tryptophan. The group of amino acids having uncharged polar side chains comprises asparagine, glutamin, tyrosine, cysteine, and cystine. The physico-chemical group of amino acids having a positively charged polar side chain comprises lysine, arginine, and histidine. The physico-chemical group of amino acids having a negatively charged polar side chain comprises aspartic acid and glutamic acid, also referred to as aspartate and glutamate.

According to the present invention, an antibody specific for LPS of the P. aeruginosa serotype IATS O6 is provided as outlined above. According to a further embodiment the present invention provides a human monoclonal antibody specific for LPS or the P. aeruginosa LPS serotype IATS O6 wherein the variable region of the light chain of the antibody has the amino acid sequence of SEQ ID NO:7 and the variable region of the heavy chain has the amino acid sequence of SEQ ID NO:8; or a variant of said antibody capable of binding said LPS wherein the variable region of the amino acid sequence of the light chain of the antibody is at least 85% homologous to SEQ ID NO:7 and the amino acid sequence of the variable region of the heavy chain of the antibody is at least 85% homologous to SEQ ID NO:8.

The term "homology" known to the person skilled in the art designates the degree of relatedness between two or more polypeptide molecules, which is determined by the agreement between the sequences. The percentage "homology" is found from the percentage of homologous regions in two or more sequences, taking account of gaps or other sequence features.

The homology of mutually related polypeptides can be determined by means of known procedures. As a rule, special computer programs with algorithms taking account of the special requirements are used. Preferred procedures for the determination of homology firstly generate the greatest agreement between the sequences studied. Computer programs for the determination of the homology between two sequences include, but are not limited to, the GCG program package, including GAP (Devereux J et al., Nucleic Acids Research 12 (12): 387 (1984); Genetics Computer Group University of Wisconsin, Madison(Wis.); BLASTP, BLASTN and FASTA (Altschul S et al., J. Molec. Biol. 215:403-410 (1990)). The BLAST X program can be obtained from the National Centre for Biotechnology Information (NCBI) and from other sources (BLAST Handbook, Altschul S et al., NCB NLM NIH Bethesda Md. 20894; Altschul S et al., J. Mol. 215; 403-410 (1990). The well-known Smith Waterman algorithm can also be used for the determination of homology.

Preferred parameters for the sequence comparison include the following:

| | |
|---|---|
| Algorithm: | Needleman and Wunsch, J. Mol. Bio. 48 (1970), 443-453 |
| Comparison matrix: | BLOSUM62 from Henikoff & Henikoff, PNAS USA 89 (1992), 10915-10919 |
| Gap penalty: | 12 |
| Gap-length penalty: | 2 |

The GAP program is also suitable for use with the above parameters. The above parameters are the standard parameters (default parameters) for amino acid sequence comparisons, in which gaps at the ends do not decrease the homology value. With very small sequences compared to the reference sequence, it can further be necessary to increase the expectancy value to up to 100,000 and in some cases to reduce the word length (word size) to down to 2.

Further model algorithms, gap opening penalties, gap extension penalties and comparison matrices including those named in the Program Handbook, Wisconsin Package, Version 9, September 1997, can be used. The choice will depend on the comparison to be performed and further on whether the comparison is performed between sequence pairs, where GAP or Best Fit are preferred, or between one sequence and a large sequence database, where FASTA or BLAST are preferred.

An agreement of 85% determined with the aforesaid algorithms is described as 85% homology. The same applies for higher degrees of homology.

In preferred embodiments, the muteins according to the invention have a homology of 85% or more, e.g. more than 90% or 95%.

It is further preferred that the light chain of the human monoclonal antibody according to the present invention is of the kappa or lambda type. Particularly preferred, the light chain is of the kappa type. The light chain may be either a naturally occurring chain including a naturally rearranged, a genetically modified or synthetic type of light chain. If the antibody according to the present invention being specific to IATS O6 is of the kappa type, then it is preferred that the light chain be derived from germ line L12a (found at URL: vbase.mrc-cpe.cam.ac.uk/index.php?module=pagemaster&PAGE_user_op=view_page&PAGE_id=15&MMN_position=11:11).

According to a further preferred embodiment, the heavy chain of the human monoclonal antibody of the present invention is selected from all human isotypes, namely IgM, IgA, or IgG. Preferably, the heavy chain is of the IgM type. If the antibody is of the IgM type, then it exhibits the advantageous properties of high avidity for $P.$ $aeruginosa$ LPS, effectively binds complement and thus mediates either direct killing of bacteria, and/or efficiently opsonizes bacteria for phagocytosis. Further, IgM is resistant to the proteolytic degradation by $P.$ $aeruginosa$ elastase, whereas other isotypes like IgG or IgA can be degraded. IgM antibodies are effective in low amounts. 1 to 4 pg per mouse were fully protective in the murine burn wound sepsis model.

It is preferred that the variable heavy chain be derived from germ line DP-75 (found at URL: vbase.mrc-cpe.cam.ac.uk/index.php?module=pagemaster&PAGE_user_op=view_page&PAGE_id=15&MMN_position=11:11).

The light chain and heavy chain may either be covalently linked as a single-chain antibody (e.g. bivalent scFv, bifunctional scFv and bispecific scFv) or non-covalently linked with each other.

According to a preferred embodiment of the present invention, the human monoclonal antibody is of fully human amino acid sequence.

"Consists entirely of human amino acid sequence" means that the amino acid sequence of the human monoclonal antibody is derived from a human germ line. This may be obtained in different ways. For example, the human monoclonal antibody consisting of human amino acid sequence can be obtained from a hybridoma wherein the B-cell is a human B-cell. Alternatively, the human monoclonal antibody may be obtained by CDR grafting of the CDR regions as indicated in the claims onto available human monoclonal antibodies thereby producing a human monoclonal antibody specific for a $P.$ $aeruginosa$ LPS serotype in accordance with the present invention.

The entirely human amino acid sequence of the human monoclonal antibody prevents the occurrence of undesired adverse effects such as rejection reactions or anaphylactic shock.

Further preferred, the human monoclonal antibody exhibits essentially human antigen recognition. "Essentially human antigen recognition" means that the antigen recognition by the human monoclonal antibody according to the present invention is essentially identical to the recognition of antigen by a human healthy individual. In particular, it is required that the Fc portions of the light and heavy chain of the human monoclonal antibody are of human type in order to ensure interaction with the human complement system, and to reduce the risk of generation of so called HAMA (human anti-Mouse Antibodies).

According to a further preferred embodiment, the human monoclonal antibody of the present invention is obtainable from a human B-cell or a hybridoma obtained by fusion of said human B-cell with a myeloma or heteromyeloma cell.

Human B-cells may be obtained by immunization of healthy individuals or patients and subsequent removal of blood samples from which human B-cells can be isolated in a known manner (Current Protocols in Immunology. Chapter 7.1. Isolation of whole mononuclear cells from peripheral blood and cord blood. Published by Wiley & Sons, Eds: J C Coligan et al.) The human B-cell may be fused to a myeloma or heteromyeloma to produce a hybridoma in accordance with known techniques according to the classical Kohler and Milstein approach. Suitable myeloma cells are derivatives of P3X63 such as P3X63Ag8.653 (ATCC CRL-1580) or SP2/0 (ATCC CRL-1646). Suitable heteromyeloma cells are e.g. F3B6 (ATCC HB-8785). The resulting hybridoma may be selected according to known procedures. The hybridomas are cultured in a suitable culture medium and the produced antibody is recovered from the supernatant.

Further, the present invention provides nucleic acids encoding the heavy chain and light chain, respectively, of the human monoclonal antibody of the present invention. The nucleic acid may be a naturally occurring nucleic acid either derived from the germ line or from rearrangement occurring in B-cells, alternatively the nucleic acids may be synthetic. Synthetic nucleic acids also include nucleic acids having modified internucleoside bonds including phosphothioester to increase resistance of the nucleic acids from degradation. The nucleic acid may be genetically engineered or completely synthetically produced by nucleotide synthesis.

The present invention further provides vectors comprising at least one nucleic acid encoding the light chain of the human monoclonal antibody of the present invention and/or at least one nucleic acid encoding the heavy chain of the human monoclonal antibody of the present invention. The nucleic acids may be either present in the same vector or may be present in the form of binary vectors. The vector preferably comprises the promoter operatively linked to the nucleic acid in order to facilitate expression of the nucleic acid encoding the light and/or heavy chain. Preferably, the vector also includes an origin for replication and maintenance in a host cell. The vector may also comprise a nucleotide sequence encoding a signal sequence located 5' of the nucleic acid encoding the light chain or heavy chain. The signal sequence may facilitate secretion of the encoded chain into the medium.

Preferably, the vector is derived from adenoviruses, vaccinia viruses, baculoviruses, SV 40 viruses, retroviruses, plant viruses or bacteriophages such as lambda derivatives or M13. The particularly preferred vector is a vector containing the constant regions of human Ig heavy chains and human light chains, such as the integrated vector system for eucaryotic expression of immunoglobulins described by Persic et al (Persic et al. 1997. Gene. 187(1):9-18).

The vector may further comprise a His-tag coding nucleotide sequence resulting in the expression of a construct for producing a fusion product with a His-tag at the N-terminus of the light and/or heavy chain of the human monoclonal antibody which facilitates purification of the protein at a nickel column by chelat formation.

Further, the present invention provides host cells comprising the vector and/or the nucleic acid suitable for the expression of the vector. In the art numerous prokaryotic and eukaryotic expression systems are known wherein eukaryotic host cells such as yeast cells, insect cells, plant cells and mammalian cells, such as HEK293-cells, PerC6-cells, CHOcells, COS-cells or HELA-cells and derivatives thereof are preferred. Particularly preferred are human production cell lines. It is preferred that the transfected host cells secrete the produced antibody into the culture medium. If intracellular expression is achieved, then renaturation is performed in accordance with standard procedures such as e.g. Benetti P H et al., Protein Expr Purif Aug; 13: 283-290, (1998)

The present invention also provides methods for producing the human monoclonal antibody. In one embodiment, the human monoclonal antibody is produced by culturing the above-described hybridoma. The produced monoclonal antibody is secreted into the supernatant and can be purified from it by applying conventional chromatographic techniques.

Alternatively, the human monoclonal antibody is produced by the host cell comprising a vector according to the present invention and culturing the host cell under conditions suitable for recombinant expression of the encoded antibody chain. Preferably, the host cell comprises at least one nucleic acid encoding the light chain and at least one nucleic acid encoding the heavy chain and is capable of assembling the human monoclonal antibody such that a 3-dimensional structure is generated which is equivalent to the 3-dimensional structure of a human monoclonal antibody produced by a human B-cell. If the light chain is produced separately from the heavy chain, then both chains may be purified and subsequently be assembled to produce a human monoclonal antibody having essentially the 3-dimensional structure of a human monoclonal antibody as produced by a human B-cell.

The human monoclonal antibody may also be obtained by recombinant expression of the encoded light and/or heavy chain wherein the nucleic acid is produced by isolating a nucleic acid encoding a human monoclonal antibody in a known manner and grafting of the nucleic acid sequence encoding the CDR's as defined in the claims onto the isolated nucleic acid.

According to a further preferred embodiment, the human monoclonal antibody according to the present invention is modified. The modifications include the di-$_1$ oligo-$_1$ or polymerization of the monomeric form e.g. by cross-linking using dicyclohexylcarbodiimide. The thus produced di-$_1$ oligo-$_1$ or polymers can be separated from each other by gel filtration. Further modifications include side chain modifications, e.g. modifications of ε-amino-lysine residues, or amino and carboxy-terminal modifications, respectively. Further modifications include post-translational modifications, e.g. glycosylation and/or partial or complete deglycosylation of the protein, and disufide bond formation. The antibody may also be conjugated to a label, such as an enzymatic, fluorescent or radioactive label.

The present invention further provides pharmaceutical compositions comprising at least one human monoclonal antibody and/or at least one nucleic acid encoding a light and/or heavy chain of the human monoclonal antibody.

The pharmaceutical composition may further comprise pharmaceutical acceptable ingredients known in the art.

Preferably, the pharmaceutical compositions are applied for the treatment of diseases caused by *P. aeruginosa* in infections such as sepsis, chronic bronchitis, local infections, mainly in immunocompromised patients and/or in patients with compromised respiratory function. The pharmaceutical compositions are further intended for the prophylaxis and/or treatment of hospital-acquired (nosocomial) infections. Since the main victims of *P. aeruginosa* infections are cystic fibrosis patients, burn victims, intubated patients, patients in surgical and/or medical intensive care units, cancer and AIDS patients, immunocompromised patients, immunosuppressed patients, diabetic patients, as well as intravenous drug abusers, the pharmaceutical compositions are in particular intended for prophylaxis and/or treatment of diseases caused by *P. aeruginosa* in said group of patients.

The pharmaceutical composition may further comprise antibiotic drugs, preferably coupled to the new monoclonal antibody.

The pharmaceutical compositions comprise the new monoclonal antibody in a concentration range of 0.5-8 mg/kg body weight.

The pharmaceutical compositions may be administered in any known manner such as intravenous, intra-muscular, intradermal, subcutaneous, intra-peritoneal, topical, intra-nasal administration, or as inhalation spray.

The present invention also provides a test kit for the diagnosis of *P. aeruginosa* infections comprising at least one human monoclonal antibody of the present invention and optionally further suitable ingredients for carrying out a diagnostic test.

The test kit is suitable for the specific reliable diagnosis of a *P. aeruginosa* infection. A test assay may be based on a conventional ELISA test in liquid or membrane-bound form. The detection may be direct or indirect as known in the art wherein the antibody is optionally conjugated to an enzymatic, fluorescent or radioactive label.

The following examples illustrate the invention but are not intended to limit the scope of the present invention. Further embodiments will be apparent for the person skilled in the art when studying the specification and having regard to common general knowledge.

BRIEF DESCRIPTION OF THE FIGURES

FIG. 1 relates to DNA (SEQ ID NO: 10) and amino acid (SEQ ID NO: 8) sequence of 310BO6 heavy chain variable region.

FIG. 2 relates to DNA (SEQ ID NO: 9)and amino acid (SEQ ID NO: 7) sequence of 310BO6 kappa light chain variable region.

FIG. 3 relates to western blot analysis of the serotype-specificity of the monoclonal antibody 310BO6. FIG. 3a shows a silverstaining of LPS from different serotypes separated on SDS PAGE. FIG. 3b shows an immunoblot analysis of LPS from different serotypes separated on SDS PAGE using the monoclonal antibody 310BO6.

MATERIAL AND METHODS

Figure 4:
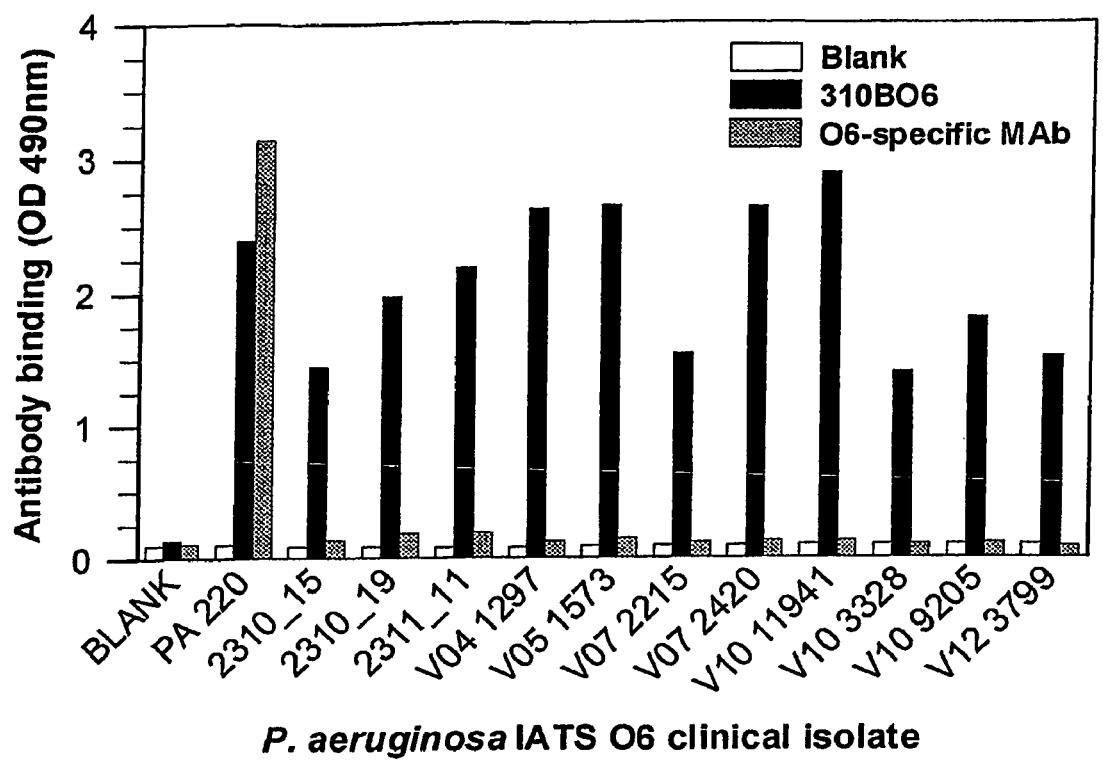
FIG. 4 relates to the recognition pattern of clinical *P. aeruginosa* isolates of the serotype IATS O6 by the monoclonal antibody 310BO6 in comparison with another IATS O6 specific monoclonal antibody.
Figure 5:
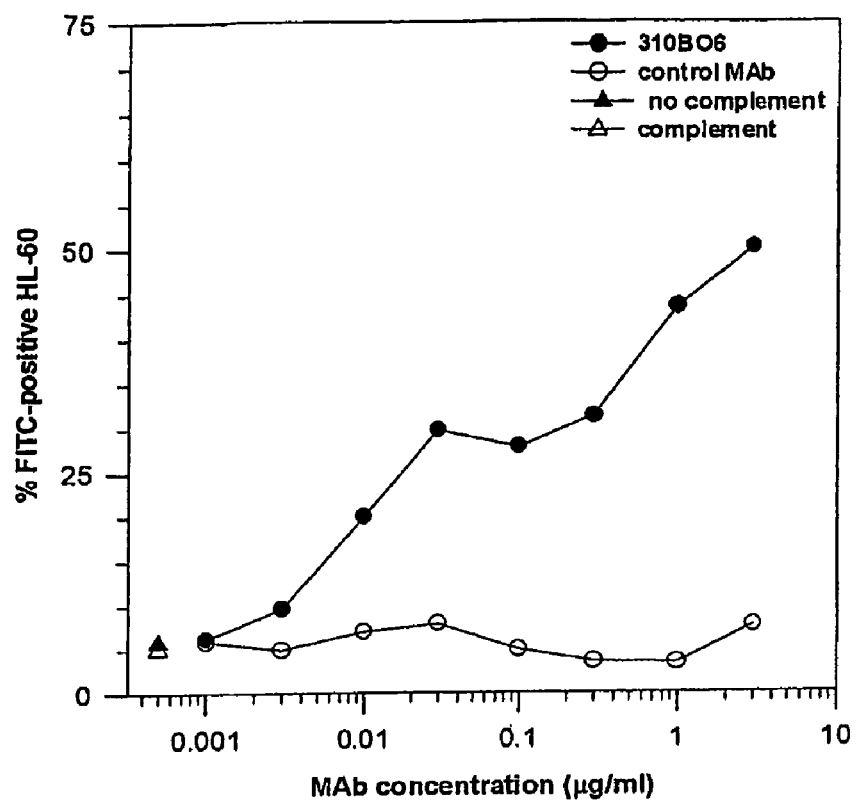
FIG. 5 relates to the opsonophagocytotic activity of the monoclonal antibody 310BO6 directed against *P. aeruginosa* serotype IATS O6.

The following Material and Methods have been used in Examples 1 to 4:

Determination of LPS-specificity and quantification of IgM in cell supernatant For screening and analysis of antibodies in cell culture supernatants, an ELISA was performed as described elsewhere (Cryz, S. J. et al., 1987. J. Clin. Invest. 80 (1):51-56) with some alterations. Briefly, *P. aeruginosa* lipopolysaccharide (produced in house) LPS stock solutions were prepared at a concentration of 2 mg/ml in 36 mM triethylamine. For coating, the solution was diluted to 10 pg/ml in PBS containing 0.02% sodium azide (PBS-Az). This solution was mixed with an equal volume of 10 llg/ml methylated human serum albumine (HSA; produced in house as follows:

29 of lyophilized HSA was dissolved in 200 ml absolute methanol. After adding 1.68 ml of 37% HCl, the solution is stored for at least 3 days at room temperature in the dark with occasional shaking. The precipitate is collected by a 10 min centrifugation (4500 rpm, GS1 rotor), and washed twice with absolute methanol and twice with anhydrous ether by suspending the pellet in the solvent. The precipitate is dried during 2 hours in a desiccator and the dry pellet is suspended in $H_2O$, and stored in aliquots at $-20°$ C. Protein concentration was 8.05 mg/ml) in PBS-Az by gently stirring for 5 minutes at room temperature. NUNC® ELISA plates were coated with 100 μl/well LPS-HSA solution over night at room temperature. After washing the plates 3× with 300 μl PBS pH 7.4 (produced in house) containing 0.05% Tween20 (#93773; Fluka Chemie AG, Switzerland) (PBS-T), cell culture supernatants were incubated 1:2 diluted in PBS for 2 hours at 37° C. After washing the plates 3× with PBS-T, bound antibodies were detected with horseradish peroxidase-conjugated goat anti-human IgM antibody (# 074-1003; KPL; Kirkegaard & Perry Laboratories, Inc. Gaithersburg, Md.) diluted 1:2000 in PBS containing 5% (v/v) FCS. The plates were incubated for 1 hour at 37° C., and washed 3× with PBS-T. Antibody-binding was visualized by adding 100 μl/well OPD (0.4 mg/ml Orthophenyldiamin in 24 mM citric acid and 52 mM di-sodium hydrogen phosphate containing 0.0012% (V/V) $H_2O_2$ substrate solution. Color reaction was stopped after 2-3 min by the addition of 50 μl/well 1 M HCl. Optical density was read on a ELISA reader at 490 nm using Softmax Pro® software.

For quantification of IgM in the cell culture supernatants, ELISA plates were coated with 1 pg/ml unconjugated goat anti-human IgM antibody in PBS over night at 4 C. Plates were washed 3× with PBS-T, and cell supernatants and standards were incubated in 2-fold dilutions. As standard human standard serum (Behring) was used starting at a concentration of 0.5 μg/ml. All dilutions were done in PBS-T. Plates were incubated for 2 hours at room temperature on a rocking table. After washing the plates 3× with PBS-T, bound antibodies were detected with horseradish peroxidase-conjugated goat anti-human IgM. antibody (KPL) diluted 1: 2000 in PBS containing 5% (v/v) FCS. The plates were incubated for 1 hour at room temperature on a rocking table, and washed 3× with PBS-T. Antibody-binding was visualized by adding 150 μl/well OPD substrate solution. Color reaction was stopped after 1 min by the addition of 50 μ/well 1 M HCl. Optical density was read on a ELISA reader at 490 nm using SoftmaxPro® software.

Sequence Analysis

RNA of hybridoma cells was isolated by using RNeasy-Kit from Qiagen. cDNA was synthesized with the SMART Technology (Becton Dickenson). For the second strand PCR the following primers were used (Table lll): (1) reverse constant IgM (conμ): 5'-GCC ACG CTG CTC GTA TCC GACG-3' (SEQ ID NO:11): (2) reverse constant Kappa (con $_κ$): 5'-AGC AGG CAC ACA ACA GAG GCA GTT CC-3' (SEQ ID NO:12). The forward primers were included in the SMART-Kit. For sequencing the following primers have been used: (3) 1 gM sequence (μ seq.): 5'-GCT GCT CGT ATC CGA CGG-3' (SEQ ID NO:13), and (4) Kappa sequence($_κ$ seq.): 5'-CAC AAC AGA GGC AGT TCC-3' (SEQ ID NO:14). Sequencing was performed at Microsynth AG (Balgach, Switzerland) and sequences were compared with existing germline sequences using the V-Base DNAplot software (found at URL: vbase.mrc-cpe.cam.ac.uk/).

Immunoblot Analysis

LPS of different serotypes (produced in house) (Table 1) were loaded on a reducing SDS-polyacrylamide gradient gel (4-15% precast gel; BioRad). After separation (15 mA/gel, 60 min+), the gel was blotted onto nitrocellulose filters and free binding sites were blocked with PBS containing 5% (V/V) FCS. The nitrocellulose was incubated in undiluted cell supernatant for 2 hours at room temperature on a rocking table. After washing 3× in PBS-T and 2× in PBS, the nitrocellulose filter was incubated with alkaline phosphatase-conjugated goat anti-human IgM antibody diluted 1:500 in PBS containing 5% (VN) FCS for 90 min at room temperature on a rocking table. After washing 3× in PBS-T and 2× in PBS, bound antibodies were visualized using BCIP/NBT (5-bromo-4-chloro-3-indoyl-phosphate/nitroblue tetrazolium) Alkaline Phosphatase substrate (KPL), and color reaction was stopped after 5 min with $H_2O$.

TABLE I

IATS Sterotypes of *P. aeruginosa* reference strains

| IATS Serotypes | Specification |
|---|---|
| 01 | PA53(IT4) |
| 02 | E576(IT3) |
| 03 | 6510(Habs3) |
| 04 | 6511(Habs4) |
| 06 | PA220(IT1) |
| 07 | Fisher 6(IT6) |
| 010 | Fisher 5(IT5) |
| 011 | Fisher 2(IT2) |
| 016 | Fisher 7(IT7) |

TABLE II

Clinical isolates of *P. aeruginosa* serotype IATS 06

| # Isolate | source of isolate |
|---|---|
| 2310_15 | cystic fibrosis |
| 2310_19 | cystic fibrosis |
| 2311_11 | Broncho-catheter |
| V041297 | vaginal infection |
| V051573 | cystic fibrosis |
| V072215 | catheter |
| V072420 | wound |
| V1011941 | wound |
| V103328 | Lung transplantation |
| V109205 | sputum |
| V123799 | Tracheal secretion |

Whole Cell ELISA

Bacteria from different clinical isolates (see Table II) were grown in Luria broth medium at 37° C. to an optical density at 600 nm of 1, and fixed with 37% Formalin (final concentration of formalin: 0.5%) over night at 37° C. The fixed bacteria were diluted 1:50 in PBS and immobilized on ELISA plates. After blocking the plates with PBS containing 5% (v/v) fetal calf serum, the monoclonal antibody 310BO6 and another monoclonal antibody, both directed against *P. aeruginosa* serotype IATS O6, were incubated with the fixed bacteria for 2 hours at 37° C. After washing the plates 3× with PBS-T, bound antibodies were detected with horseradish peroxidase-conjugated goat anti-human IgM antibody (# 074-1003; KPL; Kirkegaard & Perry Laboratories, Inc. Gaithersburg, Md.) diluted 1:2000 in PBS containing 5% (v/v) FCS. The plates were incubated for 1 hour at 37° C., and washed 3× with PBS-T. Antibody-binding was visualized by adding 100 μl/well OPD (0.4 mg/ml Orthophenyldiamin in 24 mM citric acid and 52 mM di-sodium hydrogen phosphate containing 0.0012% (V/V) $H_2O_2$ substrate solution. Color reaction was stopped after 2-3 min by the addition of 50 µl/well 1 M HCl. Optical density was read on a ELISA reader at 490 nm using Softmax Pro® software.

Opsonophagocytosis Assay

In order to determine the biological activity, the monoclonal anti-*P. aeruginosa* LPS antibodies were tested for their opsonophagocytic activity. For this purpose, *P. aeruginosa* bacteria of the serotype IATS O6, according to table 1, were grown in TSBG (30 g/l Tryptic Soy Broth containing 1% (w/v) Glucose) medium overnight. After washing twice the bacteria with cold PBS, the bacterial pellet was re-suspended in 5 ml 0.1 M Bi-Carbonate buffer, pH8.0. 50 µl of 5-(and-6)-carboxyfluorescein, succinimidyl ester (5(6)-FAM, SE; Molecular Probes, Eugene, Oreg.; 10 mg/ml in Dimethylsulfoxid) were added, and incubated at 37° C. for 1 hour. Bacteria were fixed by the addition of 100 µl 37% Formaldehyde and incubation over night at 37° C. To remove the unconjugated dye, bacteria were washed 6 times by centrifugation re-suspension in 20 ml cold sterile PBS. The labeled bacteria were stored at 4° C. until use. For the assay, an aliquot of the bacteria was diluted to an optical density at 550 nm of 1, followed by a 1:50 dilution HBSS-BSA (Hanks balanced salt solution containing 0.1% BSA). 20 µl of the bacteria were mixed with 10 µl of different dilutions of hybridoma cell culture supernatant containing the monoclonal antibody 310BO6, or a non-specific monoclonal control antibody respectively. After 30 min incubation at 37° C., 10 µl of baby rabbit serum (Charles River Laboratories, Germany) was added as a source of complement, and the probes were incubated for another 30 min at 37° C. 40 µl of differentiated HL-60 cells (the promyelocytic cell line HL-60 was differentiated into granulocytic cells by incubating the cells for 3 days in Iscoves Modified Dulbecco's Medium (lMDM; Sigma) supplemented with 10% (v/v) Fetal Calf Serum and 100 mM di-methyl-formamide) were added to the opsonized bacteria to obtain a final concentration of $1.25 \times 10^6$ cells/ml. After incubating for 90 min at 37° C. on a shaker, the cells were harvested by transferring to 2 ml of cell wash buffer (PBS-containing 0.02% (v/v) azide; Becton Dickenson). After centrifugation for 5 min at 250×g, the cell pellet was re-suspended in 150 µl Cell wash buffer and analyzed by flow cytometry. Positive opsonophagocytotic activity was determined by analyzing the green fluorescence of the HL-60 cells in comparison with background staining. Background staining was determined by incubating fluorescein-conjugated bacteria in the presence of complement with HL-60 cells.

In vivo Protection of *P. aeruginosa* Infected Mice

The in vivo protective capacity of monoclonal anti-*P. aeruginosa* LPS antibodies was determined in the murine burn wound sepsis model. NMRI-Mice (18-20 g; Charles River Laboratories) received approximately 1 to 5 µg in a volume of 0.2 ml of the monoclonal antibodies intravenously 4 hours prior to challenge. As control, 0.2 ml of specific antibody supernatant was injected. For challenge, groups of 5 female mice were anesthetized in an atmosphere of 3-chloro-1,1,2-trifluoroethyl-difluoromethy-ether (Ethrane, Abbott Lab., Chicago, Ill.). The mice were subjected to a 10 second ethanol burn over a 2 cm² area of the back. Different concentrations (in the range of 70 cfu/mouse to 70,000 cfu/mouse) of the challenge organisms (*P. aeruginosa* IATS O6; Strain PA220; see Table 1) suspended in 0.5 ml PBS were injected immediately subcutaneously into the burned area. The animals were observed for 5 to 7 days. Protective capacity was determined by dividing the $LD_{50}$ of protected mice by the $LD_{50}$ of control mice receiving the non-specific antibody supernatant.

EXAMPLE 1

DNA and Amino Acid Sequences of 310BO6

The antibody specificity is determined by the DNA-and amino acid-sequence, respectively. DNA sequences of the variable fragments of the heavy and light chains were determined. Briefly, total RNA of the hybridoma cells was isolated, and reverse transcribed into complete cDNA using the SMART technology. By this approach, a universal primer was added at the 5' end of the cDNA. Using this primer and the Cκ and Cµ-specific primers depicted in Table III, the IgM and Kappa variable regions and constant regions were amplified by PCR. The PCR fragments were then cleaned up by excision from agarose-gels, and used as templates for sequencing with the primers depicted in Table III.

TABLE III

Primers used for PCR-amplification and sequencing of the variable regions of 1gM heavy chains and Kappa light chains of 310BO6 and 1BO11

| Primer | Sequence | Application |
|---|---|---|
| Con µ | 5'-GCCACGCTG CTCGTATCCGACG-3' (SEQ ID NO:11) | PCR |
| Con κ | 5'-AGCAGG CACACAACAGAGGCAGT-TCC-3' (SEQ ID NO:12) | PCR |
| µ seq. | 5'-GCTGCTCGTATCCGACGG-3' (SEQ ID NO:13) | Sequencing |
| κ seq. | 5'-CAC AAC AGA GGC AGT TCC-3' (SEQ ID NO:14) | Sequencing |

The sequences of the variable regions were subsequently compared with the Vbase Index. The results of the comparison with germline sequences are expressed as numbers of "replacement and silent" mutations (R:S), as depicted in Table IV. The DNA sequences and amino acid sequences are depicted in FIGS. 1 and 2.

TABLE IV

Ratio replacement vs. silent mutations from germline sequences

| | Heavy chain | | Light chain | |
|---|---|---|---|---|
| | Germline | R:S | Germline | R:S |
| 310BO6 | DP-75 | 11:5 | L12a | 2:4 |

EXAMPLE 2

Western Blot Analysis

The monoclonal antibody directed against *P. aeruginosa* LPS serotype IATS O6 was tested for its monoreactivity by Western blot analysis. LPS preparations of *P. aeruginosa* of different serotypes as depicted in Table 1 were separated by reducing SDS-PAGE, and blotted onto nitrocellulose membranes. The membranes were incubated with the hybridoma cell culture supernatant containing 310BO6 monoclonal antibody directed against *P. aeruginosa* serotype IATS O6, and bound antibodies were detected by alkaline phosphate conjugated goat anti-human IgM antibody and color substrate. As shown in FIG. 3, the monoclonal antibody 310BO6 only reacts with the LPS of serotype IATS O6.

EXAMPLE 3

Recognition of Clinical Isolates of *P. aeruginosa* Serotype IATS O6 by Monoclonal Antibody 310BO6

In comparison to another human monoclonal antibody against *P. aeruginosa* serotype IATS O6, 310BO6 recognizes a wide range of clinical isolates of *P. aeruginosa* serotype IATS O6, belonging to different suptypes of IATS O6. As demonstrated in FIG. 4 in a whole cell ELISA, 310BO6 strongly recognized all clinical isolates tested, whereas the further antibody selectively reacted with PA220. In this assay, bacteria from the different *P. aeruginosa* serotype IATS O6 isolates were used according to the methods described above.

EXAMPLE 4

In vitro Activity of 310BO6: Opsonophagocytic Activity

The protective efficacy of anti-*P. aeruginosa* LPS antibodies can be measured in vitro by the capacity to opsonize bacteria, followed by phagocytosis. For determination of the opsonizing activity of 310BO6, fluorescein-conjugated *P. aeruginosa* serotype IATS O6 (strain PA220) were incubated in the presence or absence of complement with increasing concentrations (1 ng/ml-3 μg/ml) of the monoclonal antibody 310BPO6 directed against *P. aeruginosa* serotype (ATS O6, followed by incubation with human granulocytic cells (di-methyl-formamide-differentiated HL-60 cells). These cells phagocytosed *P. aeruginosa* of serotype IATS O6 upon opsonization by 310BO6 and complement.

EXAMPLE 5

In vivo Protective Capacity of the Monoclonal Antibody 310BO6

In example 4 the in vitro effector function of the monoclonal antibody 310BO6 against *P. aeruginosa* serotype IATS O6 was demonstrated. However, an antibody with a therapeutic potential should not only be active in vitro but also in vivo. This in vivo activity of 310BO6 was demonstrated by the prevention of sepsis in the murine burn wound sepsis model. In this model, mice received hybridoma cell culture supernatant containing 5 μg of the antibody 310BO6 directed against *P. aeruginosa* serotype IATS O6 or, as a control, cell culture supernatant of another human hybridoma cell line producing a non-specific human IgM/κ antibody 4 hours prior to challenge. To induce the burn wound septic shock, mice were anesthetized, and subjected to a 10 second ethanol burn on the back. Immediately after the burn, mice were challenged with at least 3 three different logs of *P. aeruginosa* serotype IATS O6 (70 cfu/mouse-7,000 cfu/mouse in the control group receiving non-specific monoclonal antibody, and 700 cfu/mouse-70,000 cfu/mouse in the group receiving 310BO6) suspended in 0.5 ml PBS. Mice were observed for 5 to 7 days, and the protective potential of antibodies were expressed as x-fold increase in $LD_{50}$ titers of challenging bacteria (Table V). Lethal dose (50%; $LD_{50}$) was calculated according to the method of Reed and Muench (Reed, L. J. and Muench, H., 1938. Amer. J. Hyg. 27: 493) Table V.

TABLE V

| | In vivo protective potential of 310BO6 $LD_{50}$ (cfu) | | | |
|---|---|---|---|---|
| Antibody clone | Serospecificity | Control | Treated | Fold Protection |
| 310BO6 | IATS O6 | 24 | 35'541 | 1476 |

The invention claimed is:

1. A human monoclonal antibody specific for LPS of the *Pseudomonas aeruginosa* LPS serotype IATS 06, wherein the variable region of the light chain of said antibody comprises the amino acid sequence of SEQ ID NO:7 and the variable region of the heavy chain of said antibody comprises the amino acid sequence of SEQ ID NO:8, or a variant of said antibody capable of binding said LPS, wherein the amino acid sequence of the variable region of the light chain of said variant of said antibody is at least 85% homologous to SEQ ID NO:7 and the amino acid sequence of the variable region of the heavy chain of said variant of said antibody is at least 85% homologous to SEQ ID NO:8.

2. The human monoclonal antibody of claim 1, wherein the light chains are selected from the group consisting of at least one of kappa type light chains and lambda type light chains.

3. The human monoclonal antibody of claim 1, wherein the heavy chains are selected from the group consisting of IgM type heavy chains, IgA type heavy chains, or IgG type heavy chains.

4. The human monoclonal antibody of claim 3, wherein the heavy chains are IgM type heavy chains.

5. The human monoclonal antibody of claim 1, wherein said antibody consists of a human amino acid sequence.

6. The human monoclonal antibody of claim 1, wherein said antibody is from a human B cell or a hybridoma of said human B cell and a myeloma or a heteromyeloma cell.

7. A hybridoma capable of producing said human monoclonal antibody of claim 1.

8. An isolated nucleic acid encoding a light chain of a human monoclonal antibody, wherein said nucleic acid encodes a polypeptide comprising the sequence set forth in SEQ ID NO:7.

9. An isolated nucleic acid encoding a heavy chain of a human monoclonal antibody, wherein said nucleic acid encodes a polypeptide comprising the sequence set forth in SEQ ID NO:8.

10. A vector comprising at least one nucleic acid selected from the group consisting of: a) an isolated nucleic acid encoding a light chain of a human monoclonal antibody, wherein said nucleic acid encodes a polypeptide comprising the sequence set forth in SEQ ID NO:7; and, b) an isolated nucleic acid encoding a heavy chain of a human monoclonal antibody, wherein said nucleic acid encodes a polypeptide comprising the sequence set forth in SEQ ID NO:8.

11. The vector of claim 10, wherein said vector further comprises a promoter operatively linked to said nucleic acid.

12. A host cell comprising said vector of claim 10.

13. A host cell comprising an isolated nucleic acid, wherein said nucleic acid is selected from the group consisting of: a) an isolated nucleic acid encoding a light chain of a human monoclonal antibody, wherein said nucleic acid encodes a polypeptide comprising the sequence set forth in SEQ ID NO:7; and, b) an isolated nucleic acid encoding a heavy chain of a human monoclonal antibody, wherein said nucleic acid encodes a polypeptide comprising the sequence set forth in SEQ ID NO:8.

14. A method for producing a human monoclonal antibody specific for LPS of the *Pseudomonas aeruginosa* LPS serotype IATS 06, said method comprising culturing said hybridoma of claim 7 under conditions for secretion of an antibody.

15. A method for producing a human monoclonal antibody specific for LPS of the *Pseudomonas aeruginosa* LPS serotvoe IATS 06, said method comprising culturing the host cell of claim 12 under conditions suitable for expression of said human monoclonal antibody.

16. A method for producing a human monoclonal antibody specific for LPS of the *Pseudomonas aeruginosa* LPS serotype IATS 06, said method comprising culturing the host cell of claim 13 under conditions suitable for expression of said human monoclonal antibody.

17. A pharmaceutical composition comprising at least one human monoclonal antibody of claim 1, said pharmaceutical composition further optionally comprising at least one pharmaceutically acceptable ingredient.

18. The pharmaceutical composition of claim 17 wherein said pharmaceutical composition further comprises at least one of a nucleic acid selected from the group consisting of: a) an isolated nucleic acid encoding a light chain of a human monoclonal antibody, wherein said nucleic acid encodes a polypeptide comprising the sequence set forth in SEQ ID NO:7; and, b) an isolated nucleic acid encoding a heavy chain of a human monoclonal antibody, wherein said nucleic acid encodes a polypeptide comprising the sequence set forth in SEQ ID NO:8, and further wherein said pharmaceutical composition optionally comprises at least one pharmaceutically acceptable ingredient.

19. A kit for the diagnosis of a *Pseudomonas aeruginosa* infection in a sample, said kit comprising at least one human monoclonal antibody of claim 1.

20. The kit of claim 19, said kit further comprising at least one nucleic acid selected from the group consisting of: a) an isolated nucleic acid encoding a light chain of a human monoclonal antibody, wherein said nucleic acid encodes a polypeptide comprising the sequence set forth in SEQ ID NQ:7; and, b) an isolated nucleic acid encoding a heavy chain of a human monoclonal antibody, wherein said nucleic acid encodes a polypeptide comprising the sequence set forth in SEQ ID NO:8.

21. A kit for the diagnosis of a *Pseudomonas aeruginosa* infection in a sample, said kit comprising at least one human monoclonal antibody of claim 1, and at least one nucleic acid selected from the group consisting of: a) an isolated nucleic acid encoding a light chain of a human monoclonal antibody, wherein said nucleic acid encodes a polypeptide comprising the sequence set forth in SEQ ID NQ:7: and, b) an isolated nucleic acid encoding a heavy chain of a human monoclonal antibody, wherein said nucleic acid encodes a polypeptide comprising the sequence set forth in SEQ ID NQ:8.

* * * * *

SEQUENCE LISTING

<160> NUMBER OF SEQ ID NOS: 14

<210> SEQ ID NO 1
<211> LENGTH: 16
<212> TYPE: PRT
<213> ORGANISM: Homo sapiens

<400> SEQUENCE: 1

Arg Ala Ser Gln Ser Ile Ser Ser Trp Leu Ala Trp Tyr Gln Gln Lys
1               5                   10                  15

<210> SEQ ID NO 2
<211> LENGTH: 7
<212> TYPE: PRT
<213> ORGANISM: Homo sapiens

<400> SEQUENCE: 2

```
Lys Ala Ser Ser Leu Glu Ser
1               5

<210> SEQ ID NO 3
<211> LENGTH: 9
<212> TYPE: PRT
<213> ORGANISM: Homo sapiens

<400> SEQUENCE: 3

Cys Gln Gln Tyr Lys Ser Tyr Pro Val
1               5

<210> SEQ ID NO 4
<211> LENGTH: 5
<212> TYPE: PRT
<213> ORGANISM: Homo sapiens

<400> SEQUENCE: 4

Gly Tyr Trp Met His
1               5

<210> SEQ ID NO 5
<211> LENGTH: 17
<212> TYPE: PRT
<213> ORGANISM: Homo sapiens

<400> SEQUENCE: 5

Arg Ile Asn Pro Asn Ser Gly Gly Thr Lys Tyr Val Gln Lys Phe Gln
1               5                   10                  15

Gly

<210> SEQ ID NO 6
<211> LENGTH: 15
<212> TYPE: PRT
<213> ORGANISM: Homo sapiens

<400> SEQUENCE: 6

Ala Arg Pro Gly Cys Gly Gly Asp Cys Tyr Glu Val Leu Asp Tyr
1               5                   10                  15

<210> SEQ ID NO 7
<211> LENGTH: 107
<212> TYPE: PRT
<213> ORGANISM: Homo sapiens

<400> SEQUENCE: 7

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Ser Tyr Pro Val
                85                  90                  95

Phe Gly Gln Gly Thr Lys Val Glu Ile Lys Gly
                100                 105
```

<210> SEQ ID NO 8
<211> LENGTH: 124
<212> TYPE: PRT
<213> ORGANISM: Homo sapiens

<400> SEQUENCE: 8

Gln Ala Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Ile Gly Tyr
            20                  25                  30
Trp Met His Trp Val Arg Gln Ala Pro Gly Gln Gly Pro Glu Trp Met
        35                  40                  45
Gly Arg Ile Asn Pro Asn Ser Gly Gly Thr Lys Tyr Val Gln Lys Phe
    50                  55                  60
Gln Gly Arg Val Thr Val Thr Arg Asp Thr Ser Ile Ser Thr Ala Tyr
65                  70                  75                  80
Met Glu Leu Asn Trp Leu Thr Ser Asp Asp Thr Ala Val Tyr Tyr Cys
                85                  90                  95
Ala Arg Ala Arg Pro Gly Cys Gly Gly Asp Cys Tyr Glu Val Leu Asp
            100                 105                 110
Tyr Trp Gly Gln Gly Thr Leu Val Thr Val Ser Ser
        115                 120

<210> SEQ ID NO 9
<211> LENGTH: 321
<212> TYPE: DNA
<213> ORGANISM: Homo sapiens

<400> SEQUENCE: 9
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaagctctt gatctataag gcatctagtt tagaaagtgg ggtcccatca     180
aggttcagcg gcagtggatc tgggacagaa ttcactctca ccattagcag cctgcagcct     240
gatgattttg caacttatta ctgccaacag tataaaagtt atcccgtgtt tggccaaggg     300
accaaggtgg aaatcaaagg a                                               321

<210> SEQ ID NO 10
<211> LENGTH: 372
<212> TYPE: DNA
<213> ORGANISM: Homo sapiens

<400> SEQUENCE: 10
caggcgcagc tggtgcagtc tggggctgaa gtgaagaagc tggggcctc agtgaaggtc       60
tcctgtaagg cttctggata caccttcatc ggctattgga tgcactgggt gcgacaggcc     120
cctggacaag ggcctgagtg gatgggacgg atcaacccta acagtggtgg cacaaagtat     180
gtacagaagt tcagggcag ggtcaccgtg accagggaca cgtccatcag cacagcctac      240
atggagctga actggctgac atctgacgac acggccgtct attactgtgc gagagcaagg     300
cctggttgtg gtggtgattg ctatgaggtc ttagattact ggggccaggg aaccctggtc     360
accgtctcct ca                                                         372

<210> SEQ ID NO 11
<211> LENGTH: 22
<212> TYPE: DNA
<213> ORGANISM: Artificial Sequence -continued

```
<220> FEATURE:
<223> OTHER INFORMATION: Chemically Synthesized Primer

<400> SEQUENCE: 11
gccacgctgc tcgtatccga cg                                    22

<210> SEQ ID NO 12
<211> LENGTH: 26
<212> TYPE: DNA
<213> ORGANISM: Artificial Sequence
<220> FEATURE:
<223> OTHER INFORMATION: Chemically Synthesized Primer

<400> SEQUENCE: 12
agcaggcaca caacagaggc agttcc                                26

<210> SEQ ID NO 13
<211> LENGTH: 18
<212> TYPE: DNA
<213> ORGANISM: Artificial Sequence
<220> FEATURE:
<223> OTHER INFORMATION: Chemically Synthesized Primer

<400> SEQUENCE: 13
gctgctcgta tccgacgg                                         18

<210> SEQ ID NO 14
<211> LENGTH: 18
<212> TYPE: DNA
<213> ORGANISM: Artificial Sequence
<220> FEATURE:
<223> OTHER INFORMATION: Chemically Synthesized Primer

<400> SEQUENCE: 14
cacaacagag gcagttcc                                         18
```